(12) United States Patent
Kongguillermo

(10) Patent No.: US 12,376,724 B2
(45) Date of Patent: Aug. 5, 2025

(54) DUST COLLECTING DEVICE

(71) Applicant: Jennifer Kongguillermo, Pembroke, GA (US)

(72) Inventor: Jennifer Kongguillermo, Pembroke, GA (US)

( * ) Notice: Subject to any disclaimer, the term of this patent is extended or adjusted under 35 U.S.C. 154(b) by 352 days.

(21) Appl. No.: 17/979,620

(22) Filed: Nov. 2, 2022

(65) Prior Publication Data

US 2024/0138648 A1 May 2, 2024

(51) Int. Cl.
| | |
|---|---|
| A47L 13/52 | (2006.01) |
| A46B 5/00 | (2006.01) |
| A46B 17/00 | (2006.01) |
| A47L 13/17 | (2006.01) |
| A61L 2/18 | (2006.01) |
| A61L 2/26 | (2006.01) |

(52) U.S. Cl.
CPC ............... *A47L 13/52* (2013.01); *A46B 5/00* (2013.01); *A46B 17/00* (2013.01); *A47L 13/17* (2013.01); *A61L 2/18* (2013.01); *A61L 2/26* (2013.01); *A46B 2200/302* (2013.01); *A61L 2202/17* (2013.01)

(58) Field of Classification Search
CPC . A47L 13/52; A47L 13/17; A61L 2/18; A61L 2/26; A61L 2202/17; A46B 2200/302
See application file for complete search history.

(56) References Cited

U.S. PATENT DOCUMENTS

| | | | |
|---|---|---|---|
| 6,681,434 B2 * | 1/2004 | Smith | A47L 13/17 |
| | | | 15/118 |
| 10,016,054 B1 * | 7/2018 | Parasher | A47L 13/16 |
| 2003/0019065 A1 * | 1/2003 | Smith | A47L 13/20 |
| | | | 15/228 |
| 2009/0144926 A1 * | 6/2009 | Fava | A47L 13/44 |
| | | | 15/228 |
| 2011/0146018 A1 * | 6/2011 | Vasilakes | A47L 13/11 |
| | | | 15/231 |

FOREIGN PATENT DOCUMENTS

| | | | | |
|---|---|---|---|---|
| CA | 2221918 C | * | 7/2001 | ......... B65D 83/0805 |
| CN | 2857617 Y | * | 1/2007 | ........... A46B 5/0095 |
| CN | 108742393 A | * | 11/2018 | |
| EP | 0744357 A1 | * | 11/1996 | |
| JP | 10155714 A | * | 6/1998 | |

* cited by examiner

*Primary Examiner* — Marc Carlson
(74) *Attorney, Agent, or Firm* — The Iwashko Law Firm, PLLC; Lev Ivan Gabriel Iwashko

(57) ABSTRACT

A dust collecting device removably connected to at least a portion of a broom, the dust collecting device including a main body to at least partially cover a broomstick of the broom, at least one disinfecting wipe disposed within at least a portion of the main body to cleanse an external surface in response to moving across the external surface and prevent a trail of debris, and a broom receiving groove disposed on at least a portion of the main body to connect the main body to the broomstick of the broom.

6 Claims, 2 Drawing Sheets

DUST COLLECTING DEVICE

BACKGROUND

1. Field

The present general inventive concept relates generally to cleaning, and particularly, to a dust collecting device.

2. Description of the Related Art

Cleaning is a means of sanitizing an object and/or an area. Moreover, cleaning is an important process to maintain proper hygienic conditions.

Some methods of cleaning use a traditional dustpan and a broom to sweep away dirt and/or debris. However, using the dustpan and the broom often leaves behind a trail of the debris which can be highly inefficient and ineffective. Furthermore, current designs of dust pans are bulky, easy to break, and/or difficult to use as a complement to the broom.

Therefore, there is a need for a dust collecting device that removes dirt and/or debris without leaving the trail of the debris.

SUMMARY

The present general inventive concept provides a dust collecting device.

Additional features and utilities of the present general inventive concept will be set forth in part in the description which follows and, in part, will be obvious from the description, or may be learned by practice of the general inventive concept.

The foregoing and/or other features and utilities of the present general inventive concept may be achieved by providing a dust collecting device removably connected to at least a portion of a broom, the dust collecting device including a main body to at least partially cover a broomstick of the broom, at least one disinfecting wipe disposed within at least a portion of the main body to cleanse an external surface in response to moving across the external surface and prevent a trail of debris, and a broom receiving groove disposed on at least a portion of the main body to connect the main body to the broomstick of the broom.

The at least one disinfecting wipe may be wet.

The broom receiving groove may use an adhesive thereon to fasten the main body to the broom.

The dust collecting device may further include a wipe extraction aperture disposed on at least a portion of the main body to facilitate removal of the at least one disinfecting wipe.

The wipe extraction aperture may include a plurality of teeth to restrict entry of air into the main body and hold the at least one disinfecting wipe therebetween.

The dust collecting device may further include a lid movably connected to at least a portion of the main body to allow access to the at least one disinfecting wipe through the wipe extraction aperture while opened and prevent access to the at least one disinfecting wipe through the wipe extraction aperture while closed.

The dust collecting device may further include a latch movably disposed on at least a portion of the main body to prevent the main body from falling off the broom while closed, and allow the main body to be removed from the broom while opened.

BRIEF DESCRIPTION OF THE DRAWINGS

These and/or other features and utilities of the present generally inventive concept will become apparent and more readily appreciated from the following description of the embodiments, taken in conjunction with the accompanying drawings of which.

DETAILED DESCRIPTION

Various example embodiments (a.k.a., exemplary embodiments) will now be described more fully with reference to the accompanying drawings in which some example embodiments are illustrated. In the figures, the thicknesses of lines, layers and/or regions may be exaggerated for clarity.

Accordingly, while example embodiments are capable of various modifications and alternative forms, embodiments thereof are shown by way of example in the figures and will herein be described in detail. It should be understood, however, that there is no intent to limit example embodiments to the particular forms disclosed, but on the contrary, example embodiments are to cover all modifications, equivalents, and alternatives falling within the scope of the disclosure. Like numbers refer to like/similar elements throughout the detailed description.

It is understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art. However, should the present disclosure give a specific meaning to a term deviating from a meaning commonly understood by one of ordinary skill, this meaning is to be taken into account in the specific context this definition is given herein.

LIST OF COMPONENTS

Dust Collecting Device 100
Main Body 110

Disinfecting Wipe 120
Wipe Extraction Aperture 130
Lid 140
Broom Receiving Groove 150
Latch 160

Figure 1:
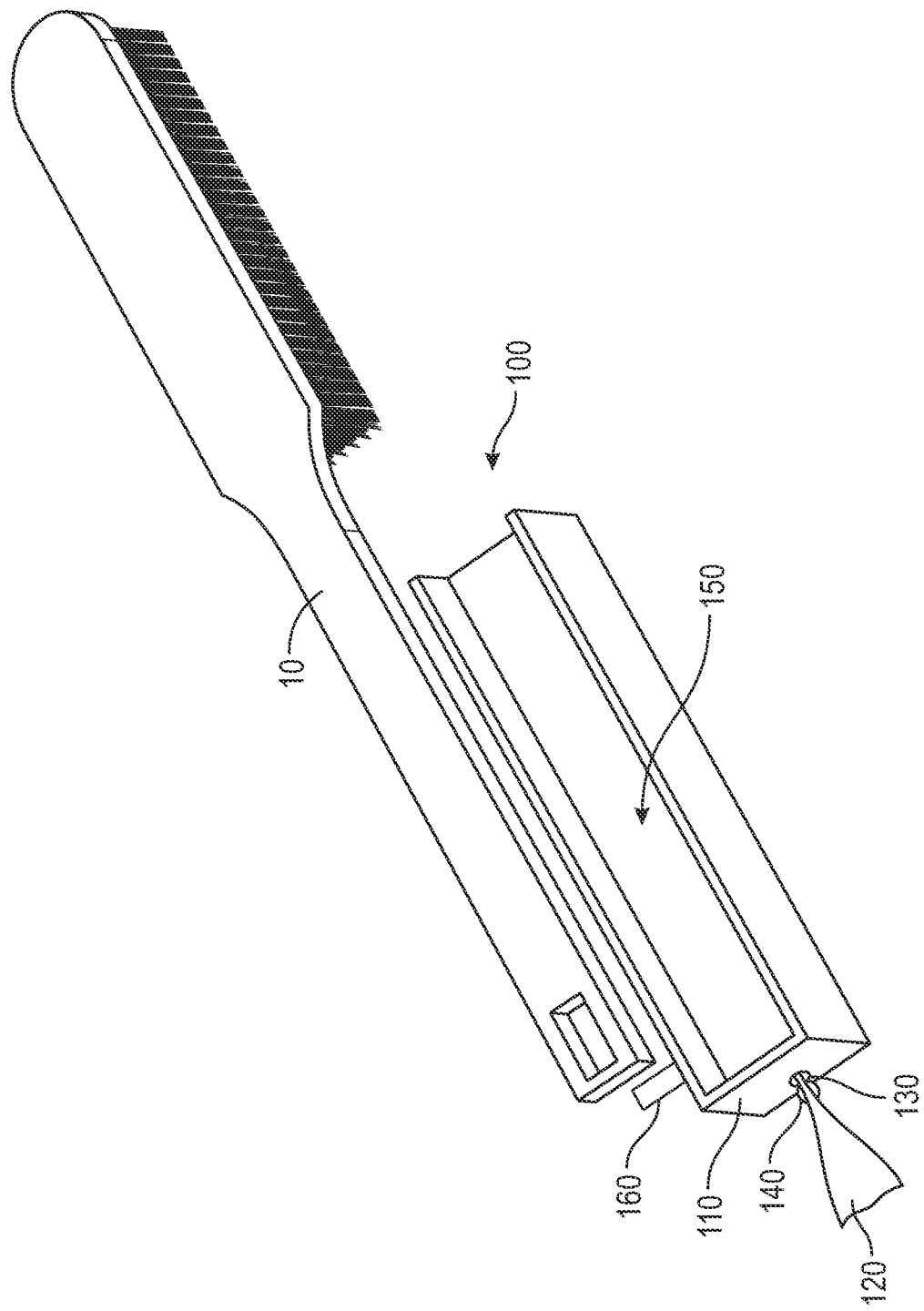
FIG. 1 illustrates an isometric top view of a dust collecting device, according to an exemplary embodiment of the present general inventive concept.

FIG. 1 illustrates an isometric top view of a dust collecting device 100, according to an exemplary embodiment of the present general inventive concept.

Figure 2:
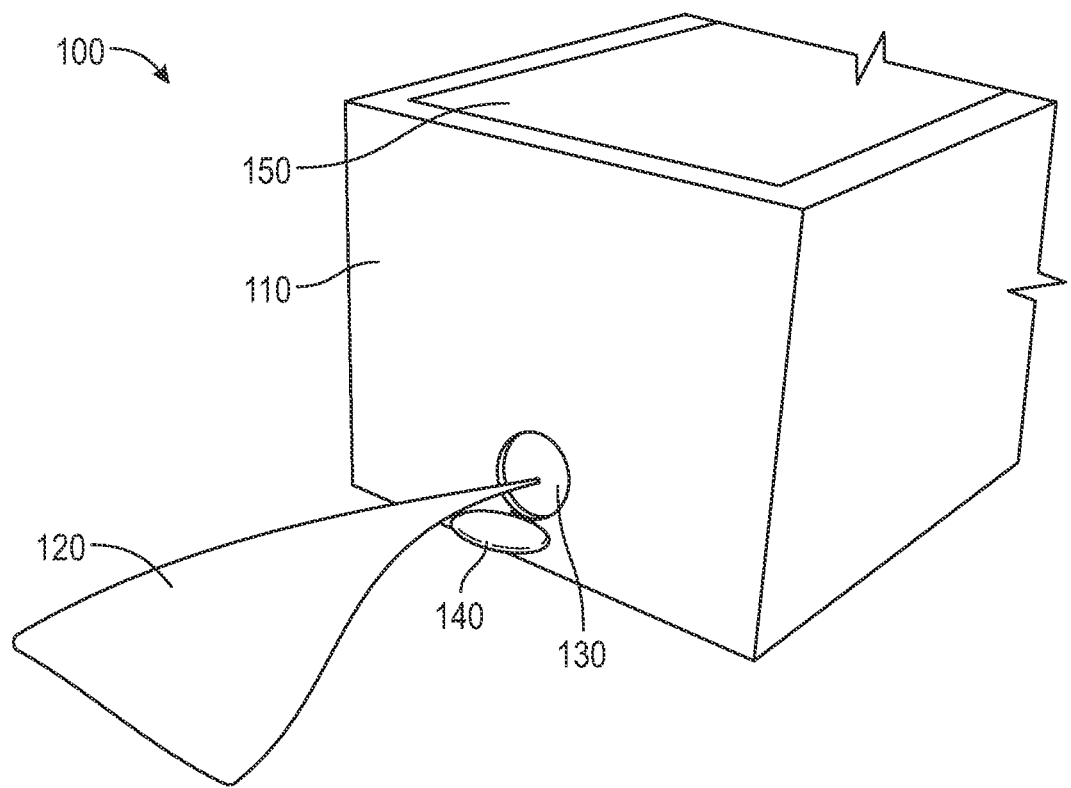
FIG. 2 illustrates a zoomed in view of a wipe extraction aperture, according to an exemplary embodiment of the present general inventive concept.

FIG. 2 illustrates a zoomed in view of a wipe extraction aperture 130, according to an exemplary embodiment of the present general inventive concept.

The dust collecting device 100 may be constructed from at least one of metal, plastic, wood, and rubber, etc., but is not limited thereto.

The dust collecting device 100 may include a main body 110, at least one disinfecting wipe 120, a wipe extraction aperture 130, a lid 140, a broom receiving groove 150, and a latch 160, but is not limited thereto.

Referring to FIGS. 1 and 2, the main body 110 is illustrated to have a rectangular prism shape. However, the main body 110 may be rectangular, circular, cylindrical, triangular, pentagonal, hexagonal, heptagonal, octagonal, or any other shape known to one of ordinary skill in the art, but is not limited thereto.

The main body 110 may be removably connected to at least a portion of a broom 10. More specifically, the main body 110 may connect to a broomstick of the broom 10. As such, the main body 110 may at least partially cover the broomstick of the broom 10.

The at least one disinfecting wipe 120 may be constructed from recycled material, paper, and/or cotton, but is not limited thereto.

The at least one disinfecting wipe 120 may have a cleaning agent (e.g., soap, alcohol, ethyl alcohol, ammonium, disinfectant) disposed and/or integrated thereon. Also, the at least one disinfecting wipe 120 may have at least one scent and/or fragrance emanating therefrom. As such, the at least one disinfecting wipe 120 may be wet and/or moist.

The at least one disinfecting wipe 120 may be disposed within at least a portion of an interior of the main body 110. Moreover, the at least one disinfecting wipe 120 may be extracted from the main body 110 and disposed around an outer surface of the main body 110 to be moved against an external surface (e.g., a ground surface, a table, a countertop, a desk, etc.) to cleanse the external surface in response to moving across the external surface. As a result of the wet characteristic of the at least one disinfecting wipe 120, dust, dirt, and/or debris may be prevented from leaving a trail.

The wipe extraction aperture 130 may be disposed on at least a portion of the main body 110. The wipe extraction aperture 130 may facilitate removal of the at least one disinfecting wipe 120. Additionally, the wipe extraction aperture 130 may have a plurality of slits and/or teeth to restrict entry of air into the main body 110. Also, the wipe extraction aperture 130 may hold the at least one disinfecting wipe 120 between the plurality of slits and/or teeth.

The lid 140 may be movably (i.e., slidably, hingedly) connected to at least a portion of the main body 110. The lid 140 may move from closed over the wipe extraction aperture 130 in a first position to at least partially opened away from the wipe extraction aperture in a second position. Conversely, the lid 140 may move from opened away from the wipe extraction aperture 130 in the first position to closed over the wipe extraction aperture 130 in the second position. As such, the lid 140 may allow access to the at least one disinfecting wipe 120 while opened and prevent access to the at least one disinfecting wipe 120 while closed. Also, the lid 140 may prevent the at least one disinfecting wipe 120 from drying out while closed.

The broom receiving groove 150 may be disposed on at least a portion of the main body 110. Also, the broom receiving groove 150 may extend at least a portion of an entire length of the main body 110. The broom receiving groove 150 may connect the main body 110 to the broomstick of the broom 10.

Furthermore, the broom receiving groove 150 may have an adhesive disposed thereon. For example, the broom receiving groove 150 may have a tape and/or a glue to fasten the main body 110 to the broom 10.

The latch 160 may be movably (i.e., pivotally, hingedly) disposed on at least a portion of the main body 110. The latch 160 may move from closed over the broom receiving groove 150 in a first position to at least partially extended away from the broom receiving groove 150 in a second position. Conversely, the latch 160 may move from extended away from the broom receiving groove 150 in the second position to closed over the broom receiving groove 150 in the first position. Accordingly, the latch 160 may lock over the broom 10 while closed to prevent the main body 110 from falling off the broom 10. However, the latch 160 may unlock the broom 10 while opened, such that the main body 110 may be removed from the broom 10.

Therefore, the dust collecting device 100 may remove dirt and/or debris on the external surface while using the at least one disinfecting wipe 120. Also, the dust collecting device 100 may connect to the broom 10 without requiring use of a separate cleaning tool. The dust collecting device 100 may be useful to users who cannot use a robot cleaning tool.

The present general inventive concept may include a dust collecting device 100 removably connected to at least a portion of a broom 10, the dust collecting device 100 including a main body 110 to at least partially cover a broomstick of the broom 10, at least one disinfecting wipe 120 disposed within at least a portion of the main body 110 to cleanse an external surface in response to moving across the external surface and prevent a trail of debris, and a broom receiving groove 150 disposed on at least a portion of the main body 110 to connect the main body 110 to the broomstick of the broom 10.

The at least one disinfecting wipe 120 may be wet.

The broom receiving groove 150 may use an adhesive thereon to fasten the main body 110 to the broom 10.

The dust collecting device 100 may further include a wipe extraction aperture 130 disposed on at least a portion of the main body 110 to facilitate removal of the at least one disinfecting wipe 120.

The wipe extraction aperture 130 may include a plurality of teeth to restrict entry of air into the main body 110 and hold the at least one disinfecting wipe 120 therebetween.

The dust collecting device 100 may further include a lid 140 movably connected to at least a portion of the main body 110 to allow access to the at least one disinfecting wipe 120 through the wipe extraction aperture 130 while opened and prevent access to the at least one disinfecting wipe 120 through the wipe extraction aperture 130 while closed.

The dust collecting device 100 may further include a latch 160 movably disposed on at least a portion of the main body 110 to prevent the main body 110 from falling off the broom 10 while closed, and allow the main body 110 to be removed from the broom 10 while opened.

Although a few embodiments of the present general inventive concept have been shown and described, it will be appreciated by those skilled in the art that changes may be made in these embodiments without departing from the principles and spirit of the general inventive concept, the scope of which is defined in the appended claims and their equivalents.

The invention claimed is:

1. A dust collecting device removably connected to at least a portion of a broom, the dust collecting device comprising:
    a main body to at least partially cover a broomstick of the broom;
    at least one disinfecting wipe disposed within at least a portion of the main body to cleanse an external surface in response to moving across the external surface and prevent a trail of debris;
    a broom receiving groove disposed on at least a portion of the main body to connect the main body to the broomstick of the broom; and
    a latch movably disposed on at least a portion of the main body to prevent the main body from falling off the broom while closed, and allow the main body to be removed from the broom while opened.

2. The dust collecting device of claim 1, wherein the at least one disinfecting wipe is wet.

3. The dust collecting device of claim 1, wherein the broom receiving groove uses an adhesive thereon to fasten the main body to the broom.

4. The dust collecting device of claim 1, further comprising:
    a wipe extraction aperture disposed on at least a portion of the main body to facilitate removal of the at least one disinfecting wipe.

5. The dust collecting device of claim 4, wherein the wipe extraction aperture comprises a plurality of teeth to restrict entry of air into the main body and hold the at least one disinfecting wipe therebetween.

6. The dust collecting device of claim 5, further comprising:
    a lid movably connected to at least a portion of the main body to allow access to the at least one disinfecting wipe through the wipe extraction aperture while opened and prevent access to the at least one disinfecting wipe through the wipe extraction aperture while closed.

* * * * *